United States Patent
Helmer et al.

(10) Patent No.: US 11,590,288 B2
(45) Date of Patent: Feb. 28, 2023

(54) DRUG DELIVERY DEVICE (71) Applicant: Sanofi-Aventis Deutschland GMBH, Frankfurt am Main (DE)

(72) Inventors: Michael Helmer, Frankfurt am Main (DE); Marc Schader, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 109 days.

(21) Appl. No.: 16/339,775

(22) PCT Filed: Oct. 4, 2017

(86) PCT No.: PCT/EP2017/075256
§ 371 (c)(1),
(2) Date: Apr. 5, 2019

(87) PCT Pub. No.: WO2018/069121
PCT Pub. Date: Apr. 19, 2018

(65) Prior Publication Data
US 2019/0307961 A1 Oct. 10, 2019

(30) Foreign Application Priority Data
Oct. 13, 2016 (EP) .................................... 16193698

(51) Int. Cl.
A61M 5/31 (2006.01)
A61M 5/315 (2006.01)
(Continued)

(52) U.S. Cl.
CPC .............. A61M 5/31 (2013.01); A61M 5/178 (2013.01); A61M 5/31563 (2013.01);
(Continued)

(58) Field of Classification Search
CPC ...... A61M 2205/60; A61M 2005/2013; A61M 2005/208; A61M 5/3243;
(Continued)

(56) References Cited

U.S. PATENT DOCUMENTS 10,251,779 B2 * 4/2019 Lerner ..................... A61M 5/46
2002/0050462 A1 * 5/2002 Penney ................... B65D 85/20
206/363

(Continued)

FOREIGN PATENT DOCUMENTS

CN 1906007 1/2007
CN 101247844 8/2008
(Continued)

OTHER PUBLICATIONS

PCT International Preliminary Report on Patentability in International Appln. No. PCT/EP2017/075256, dated Apr. 16, 2019, 10 pages.
(Continued)

Primary Examiner — Bhisma Mehta
Assistant Examiner — William R Frehe
(74) Attorney, Agent, or Firm — Fish & Richardson P.C.

(57) ABSTRACT

A drug delivery device that includes a housing. The housing contains a syringe, and the syringe includes a container containing a liquid medicament. The container includes an aperture at a distal end and through which the liquid medicament can be dispensed. The syringe includes a stopper within the container. The stopper is moveable between a first longitudinal position and a second longitudinal position relative to the container, to cause dispensing of the liquid medicament through the aperture. The syringe includes at least one identifying means identifying the liquid medicament.

20 Claims, 6 Drawing Sheets (51) Int. Cl.
*A61M 5/32* (2006.01)
*A61M 5/178* (2006.01)

(52) U.S. Cl.
CPC ... *A61M 5/3202* (2013.01); *A61M 2005/3125* (2013.01); *A61M 2205/52* (2013.01); *A61M 2205/583* (2013.01); *A61M 2205/6063* (2013.01); *A61M 2205/6072* (2013.01); *A61M 2205/6081* (2013.01); *A61M 2207/00* (2013.01)

(58) Field of Classification Search
CPC ...... A61M 2005/325; A61M 2005/312; A61M 5/002; A61M 2209/06; A61B 90/90; A61B 90/92; A61B 90/94; A61B 90/96
See application file for complete search history.

(56) References Cited

U.S. PATENT DOCUMENTS

| | | | |
|---|---|---|---|
| 2004/0186437 A1 | 9/2004 | Frenette et al. | |
| 2005/0146081 A1 | 7/2005 | MacLean et al. | |
| 2006/0084925 A1 | 4/2006 | Ramsahoye | |
| 2007/0255175 A1* | 11/2007 | Sangha | A61B 10/02 600/572 |
| 2011/0004165 A1* | 1/2011 | Iio | A61M 5/24 604/197 |
| 2011/0225790 A1 | 9/2011 | Farrar et al. | |
| 2012/0037530 A1* | 2/2012 | Boyd | A61M 5/3202 206/459.5 |
| 2012/0191046 A1* | 7/2012 | Larsen | A61M 5/3202 604/192 |
| 2013/0072878 A1 | 3/2013 | Avery | |
| 2013/0267904 A1* | 10/2013 | Limaye | A61M 5/31 604/189 |
| 2013/0345641 A1* | 12/2013 | German | A61M 5/24 604/189 |
| 2015/0367082 A1* | 12/2015 | Ward | A61M 5/3202 604/198 |
| 2016/0008555 A1* | 1/2016 | Schraga | A61M 5/344 604/110 |
| 2016/0331904 A1* | 11/2016 | Huthmacher | A61M 5/326 |

FOREIGN PATENT DOCUMENTS

| | | |
|---|---|---|
| CN | 201668809 | 12/2010 |
| CN | 101977645 | 2/2011 |
| CN | 102802704 | 11/2012 |
| CN | 103153366 | 6/2013 |
| CN | 104436373 | 3/2015 |
| CN | 204445905 | 7/2015 |
| CN | 105960254 | 9/2016 |
| EP | 2253348 | 11/2010 |
| JP | 2012-529322 | 11/2012 |
| JP | 2013-533076 | 8/2013 |
| JP | 2015-512747 | 4/2015 |
| JP | 2015-536772 | 12/2015 |
| JP | 2017-504422 | 2/2017 |
| WO | WO 2004/014458 | 2/2004 |
| WO | WO 2006/117692 | 11/2006 |
| WO | WO 2009/125582 | 10/2009 |
| WO | WO 2010/142813 | 12/2010 |
| WO | WO 2012/020086 | 2/2012 |
| WO | WO 2012/020089 | 2/2012 |
| WO | WO 2012/143440 | 10/2012 |
| WO | WO 2013/116353 | 8/2013 |
| WO | WO 2013/155000 | 10/2013 |
| WO | WO 2014/095308 | 6/2014 |
| WO | WO-2015113968 A1 * 8/2015 ............ A61M 5/326 |
| WO | WO 2015/150127 | 10/2015 |
| WO | WO 2016/107922 | 7/2016 |

OTHER PUBLICATIONS

PCT International Search Report and Written Opinion in International Appln. No. PCT/EP2017/075256, dated Dec. 7, 2017, 15 pages.

\* cited by examiner

DRUG DELIVERY DEVICE

CROSS REFERENCE TO RELATED APPLICATIONS

The present application is the national stage entry of International Patent Application No. PCT/EP2017/075256, filed on Oct. 4, 2017, and claims priority to Application No. EP 16193698.4, filed on Oct. 13, 2016, the disclosures of which are incorporated herein by reference.

TECHNICAL FIELD

The present disclosure relates to a drug delivery device and a method of manufacturing a drug delivery device.

BACKGROUND

Current therapies delivered by means of self-administered injections include drugs for diabetes (both insulin and new GLP-A class drugs), migraine, hormone therapies, anticoagulants etc. Drug delivery devices such as auto-injectors aim to make self-administration of injected therapies easier for users. Auto-injectors are devices which completely or partially replace activities involved in medicament delivery of manual devices.

Some auto-injectors operate with a pre-filled cartridge or syringe system. This type of system is typically provided with a separate cartridge or syringe pre-filled with medicament. In some instances, the user must insert a pre-filled cartridge into the housing of the auto-injector before injection.

Auto-injectors may also be provided with pre-filled syringes already contained within their housing such that the user does not have the inconvenience of inserting the pre-filled syringe themselves. In this case, a pre-filled syringe is inserted into the auto-injector during assembly of said auto-injector.

During the manufacturing process of pre-filled auto-injector syringes, identical syringe packages are used for different liquid medicaments. This keeps manufacturing costs low and production efficiency high. The pre-filled syringes are inserted into auto-injectors by automated machinery.

SUMMARY

According to an aspect, there is provided a drug delivery device comprising a housing, said housing containing a syringe, wherein the syringe comprises: a container containing a liquid medicament, said container comprising an aperture at a distal end thereof and through which said liquid medicament can be dispensed; a stopper within said container, said stopper moveable between a first longitudinal position and a second longitudinal position relative to the container, to cause dispensing of said liquid medicament through said aperture; and at least one identifying means identifying the liquid medicament. By providing the syringe with an identifying means identifying the liquid medicament contained within the container, it can be easily determined following insertion of the syringe into the drug delivery device whether the correct liquid medicament is contained within said drug delivery device. This can increase the production efficiency of assembling the drug delivery devices containing the syringes, while reducing wastage and costs of manufacture.

The at least one identifying means can be arranged at a distal end of the syringe. This can allow easy identification of the liquid medicament once the syringe has been inserted into the housing of the drug delivery device.

The syringe may further comprise a needle shield, wherein the needle shield comprises a hole through which liquid medicament is to be dispensed, and the at least one identifying means may be arranged on an outer surface of the needle shield. Providing the at least identifying means arranged on an outer surface of the needle shield can allow for easy identification of the liquid medicament once the syringe has been inserted into the drug delivery device.

The outer surface of the needle shield may comprise a front face, wherein the hole is arranged on the front face, and wherein the at least one identifying means is arranged on said front face. Providing the at least identifying means arranged on the front face of the needle shield can allow for identification of the liquid medicament once the syringe has been inserted into the housing of the drug delivery device, without disassembling the drug delivery device or removing the syringe from the housing of the drug delivery device.

The at least one identifying means may comprise a tampon printed surface, for example a tampon printed surface of the needle shield. Tampon printing a surface can provide an identifying means that is relatively inexpensive. Tampon printing a surface also means that an identifying means can be provided on a standard syringe, that is without additional modification of the syringe. Unique, and therefore relatively expensive, syringes do not need to be provided for each type of liquid medicament.

The at least one identifying means may comprise a laser marked surface, for example a laser marked surface of the stopper, needle shield and/or the glass barrel. The laser marked surface may be a laser engraved surface, or a UV (ultraviolet) laser marked surface. Laser marking a surface can provide an identifying means that is relatively inexpensive. Laser marking a surface also means that an identifying means can be provided on a standard syringe, that is without additional modification of the syringe. Unique, and therefore relatively expensive, syringes do not need to be provided for each type of liquid medicament.

The at least one identifying means may comprise a pin mounted on the needle shield. Providing a pin mounted on the needle shield as the identifying means can be implemented for standard syringes having a needle shield, without modification of the syringe.

The pin may be mounted in the hole of the needle shield. This can allow for identification of a liquid medicament through the opening of the drug delivery device housing, while allowing the size of the opening to be kept small.

The pin may comprise a head and a protrusion arranged on said head, the projection configured to be mounted in the hole of the needle shield. This may be a particularly effective means of releasably attaching the pin to the needle shield.

The at least one identifying means may comprise a marking printed on the container. Providing a marking printed on the container of the syringe can provide an identifying means that is relatively inexpensive. It also means that an identifying means can be provided on a standard syringe, that is without additional modification of the syringe. Unique, and therefore relatively expensive, syringes do not need to be provided for each type of liquid medicament. Providing a marking printed on the container of the syringe can allow the identifying means to be viewed through a window of the a drug delivery device housing when the syringe is inserted into the housing, without disassembling the drug delivery device or removing the syringe from the housing.

The marking may be printed on the container using UV light. This can be a particularly cost-effective means of providing an identifying means, that can be easily applied to syringes of varying shapes.

The marking may be printed on the container by laser marking. This can be another particularly cost-effective means of providing an identifying means, that can be easily applied to syringes of varying shapes.

The marking may comprise a barcode. This is advantageous in that it can allow the identifying means to be read by a computing device or other machine, which can allow for automation of identifying the liquid medicament within the syringes.

The marking may comprise a ring arranged around an outer surface of the container. This can be a particularly cost-effective means of providing an identifying means. A ring can be relatively discrete compared to other forms of marking, and can therefore be considered unremarkable to an end user. The position of the ring may also be used to indicate to an end user whether a complete dose has been delivered during an injection procedure. Ideally the ring position is synchronized with a click signifying the end of an injection. When the click occurs at the end of an injection process, the stopper will have reached the position behind or adjacent the ring.

According to another aspect, there is provided a method of manufacturing a drug delivery device comprising a housing, said housing containing a syringe, wherein the syringe comprises: a container containing a liquid medicament, said container comprising an aperture at a distal end thereof and through which said liquid medicament can be dispensed; and a stopper within said container, said stopper moveable between a first longitudinal position and a second longitudinal position relative to the container, to cause dispensing of said liquid medicament through said aperture; wherein said method comprises: providing the syringe with at least one identifying means identifying the liquid medicament contained in the container.

According to another aspect, there is provided a method for identifying a liquid medicament contained within an aforementioned drug delivery device, the syringe comprising at least one identifying means identifying the liquid medicament, the method comprising detecting, by a sensor, the at least one identifying means, and, in response to detecting the at least one identifying means, identifying the liquid medicament using the at least one identifying means.

These as well as other advantages of various aspects of the present invention will become apparent from the embodiments described hereinafter.

BRIEF DESCRIPTION OF THE FIGURES

Exemplary embodiments are described with reference to the accompanying drawings, in which:

FIG. 4b is an isometric view of drug delivery device having a window and containing the syringe of FIG. 4a.

FIG. 5b is an isometric view of drug delivery device having a window and containing the syringe of FIG. 5a.

FIG. 6b is an isometric view of a drug delivery device having a window and containing the syringe of FIG. 6a.

Reference will now be made in detail to the embodiments, examples of which are illustrated in the accompanying drawings, wherein like reference numerals refer to like elements throughout.

DETAILED DESCRIPTION

A drug delivery device comprising a housing containing a syringe with an identifying means identifying the liquid medicament contained in the syringe and a method of manufacturing a drug delivery device are provided.

The syringe includes a container containing a liquid medicament, and a stopper within the container. The container may be a barrel, such as a glass barrel. The container comprises an aperture through which the liquid medicament is configured to be dispensed during an injection procedure. The stopper is moveable between a first position and a second position with respect to the container for dispensing the liquid medicament through the aperture.

Syringes such as those described below comprise a cannula fixedly arranged at a distal end of the container, adjacent to the aperture. While the term cannula is used throughout this description, it should be noted that a cannula is also known as a needle or hollow needle. The cannula in accordance with some embodiments is rigid, so that the cannula can penetrate the skin of a user during an injection procedure. The cannula is in fluid communication with the aperture such that movement of the stopper between the first position and the second position with respect to the container dispenses the liquid medicament through the aperture and cannula.

The syringe further comprises at least one identifying means identifying the liquid medicament contained within the syringe. A machine or a user is therefore able to easily identify the liquid medicament contained within the syringe after the manufacture of said syringe, for example during or after assembly of the drug delivery device comprising said syringe.

It is preferable that the identifying means is located on an outer surface of the syringe such that it is visible from the outside, therefore making identification of the liquid medicament easier for a machine or a user.

A drug delivery device in accordance with some aspects as described below is for hypodermic delivery of a liquid medicament to a user or patient. The drug delivery device may be a handheld drug delivery device such as an injection pen.

As an example, the handheld drug delivery device may be an auto-injector. Auto-injectors are injection devices configured to deliver a medicament to a patient that aim to make self-administration of injected therapies easier for users by completely or partially replacing activities involved in medicament delivery using conventional manual injection devices. These activities may include removal of a protective syringe cap, insertion of a needle/cannula into a patient's skin, injection of the medicament, removal of the needle/cannula, shielding of the needle/cannula and preventing reuse of the device. The auto-injector therefore overcomes many of the disadvantages of manual injection devices. Triggering may be performed by numerous means, for example a trigger button or the action of the needle/cannula reaching an injection depth.

Exemplary drug delivery devices are shown in FIGS. 2a, 2b, 4b and 5b and are discussed in more detail in the description accompanying these figures.

A syringe drug delivery device in accordance with the present disclosure contains a syringe inserted into the housing of the drug delivery device before an injection procedure. This may occur at a manufacturing site during assembly of the drug delivery device such that the drug delivery device is provided to an end user with the syringe already contained within the auto-injector. This simplifies ease of use of the drug delivery device for the end user since they do not need to insert a syringe themselves.

Figure 1:
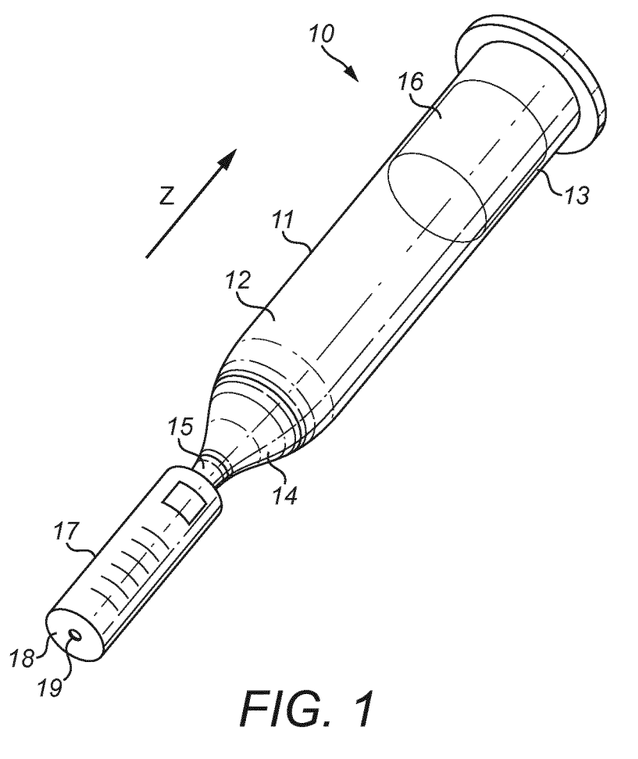
FIG. 1 is an isometric view of a syringe having a needle shield for use in a drug delivery device according to an embodiment.

According to some embodiments of the present disclosure, an exemplary syringe 10 is shown in FIG. 1. The syringe 10 is to be contained within the housing of a drug delivery device, for example the housing 21 of the drug delivery device 20 shown in FIG. 2a. The syringe 10 comprises a container 11 containing a liquid medicament 12, such that the syringe 10 is "pre-filled". The container 11 has a proximal end 13 and a distal end 14. The term "distal" as used throughout this disclosure refers to a location that is relatively closer to an injection site, and the term "proximal" refers to a location near the user during use of an auto-injector, that is relatively further away from the injection site.

The container 11 comprises an aperture 15 through which the liquid medicament 12 is dispensed. The syringe 10 further comprises a stopper or piston 16 for sealing the container 11 and displacing the liquid medicament 12 through the aperture 15. The stopper 16 is moveable within the container 11 between a first longitudinal position at the proximal end 13 of the container 11 to a second longitudinal position at the distal end 14 of the container, to displace the liquid medicament 12 out of the container 11 via the aperture 15.

The syringe 10 further comprises a cannula (not shown) arranged at the distal end 14 of the container 11, adjacent to the aperture 15.

During an injection procedure, the cannula or hollow needle is inserted into the skin of a patient such that the liquid medicament 12 contained within the container 11 of the syringe 10 may be delivered to the patient, via the cannula. As such, the cannula is configured to be in fluid communication with the container 11. The cannula may be brought into fluid communication with the liquid medicament 12 in the container 11 prior to the start of an injection procedure, for example by actuation of a mechanism arranged on the syringe or drug delivery device such as a button or sliding mechanism. Alternatively, the cannula may already be in fluid communication with the container 11 and the liquid medicament 12 in its initial state.

The syringe 10 may further comprise a needle shield 17. The needle shield 17 is configured to cover the cannula before injection, so as to prevent damage to the cannula. The needle shield 17 is arranged at the distal end 14 of the container 11, adjacent to the aperture 15 of the container 11. The needle shield 17 surrounds the cannula.

The needle shield 17 has a front face 18 at the distal end of the needle shield, the front face 18 comprising a hole 19 (otherwise referred to as a bore). The needle shield 17 is moveably attached to the container 11 such that the needle shield 17 is longitudinally moveable relative to the container 11. The needle shield 17 is moveable between a first longitudinal position and a second longitudinal position, along a longitudinal axis Z of the container 11. The needle shield 17 is moved from the first longitudinal position to the second longitudinal position by movement of the needle shield 17 toward the proximal end 13 of the container 11.

In the first longitudinal position of the needle shield 17, the cannula is substantially surrounded by the needle shield 17 such that the distal end of the cannula is within the needle shield 17, and does not extend outside the needle shield 17 via the hole 19 of the needle shield 17. The cannula is therefore protected so that it cannot be inserted into an injection site.

The needle shield 17 is moved (or retracted) to the second position prior to an injection procedure. The needle shield 17 may be physically retracted by a user, or may be retracted by actuation of a shield remover (not shown). The shield remover may be comprised in the syringe 10 or may be comprised in another part of the drug delivery device itself. In the second position of the needle shield 17, the distal end of the cannula is at least partially exposed such that the distal end of the cannula extends through the hole 19 of the needle shield 17 to the outside of the needle shield 17. The distal end of the cannula can then be inserted into an injection site. In use, liquid medicament 12 can be dispensed through the hole 19 via the cannula.

In each of the following embodiments, the syringe 10 comprises at least one identifying means identifying the liquid medicament 12 contained within the container 11 of the syringe 10. That is, a user and/or computing device is able to identify the liquid medicament 12 within the container 11 by the identifying means.

By providing the syringe with identifying means, it can be confirmed by a worker at a manufacturing site or a machine that the correct syringe containing a particular medicament has been inserted into the drug delivery device during the assembly of said drug delivery device. Previously if the medicament in the drug delivery device was not confirmed, the syringe, and perhaps the drug delivery device itself, may have been discarded. This increased wastage and the production costs of drug delivery devices.

In accordance with some embodiments, the at least one identifying means may be arranged at the distal end 14 of the syringe 10, such that the identifying means can be viewed from the distal end 14 of the syringe 10. For example, the at least one identifying means may be arranged on the front face 18 of the needle shield 17. The advantages of providing an identifying means at such a location are discussed below with reference to FIGS. 2a and 2b.

According to some aspects, the identifying means may comprise a marked surface of the syringe 10, in particular a marked outer surface of the needle shield 17. The identifying means may comprise a marked/printed surface of the syringe 10, such as a tampon printed surface. The front face 18 of the needle shield 17 may comprise the tampon printed surface.

Alternatively, or in addition, the identifying means may comprise a laser marked surface of the syringe 10. In other words, the identifying means may comprise a surface marked by a laser. In some examples the laser marked surface is a UV (ultraviolet) laser marked surface of the syringe 10. In other examples the laser marked surface is a laser engraved surface of the syringe 10.

The laser marked surface may be a laser marked surface of the stopper 16, such as the radial outer surface of the stopper 16, or a laser marked surface of the container 11 as will be discussed later.

The laser may mark the surface with a machine-readable code, such as a barcode, a QR code or Data Matrix. The front face 18 of the needle shield 17 may comprise the laser marked surface of the syringe 10. Where the syringe 10 comprises a needle shield 17, it is particularly advantageous to provide the identifying means such as the marked/printed surface on the front face 18 of the needle shield 17, around the hole 19 of the needle shield 17, as will be discussed below.

Figure 2A:
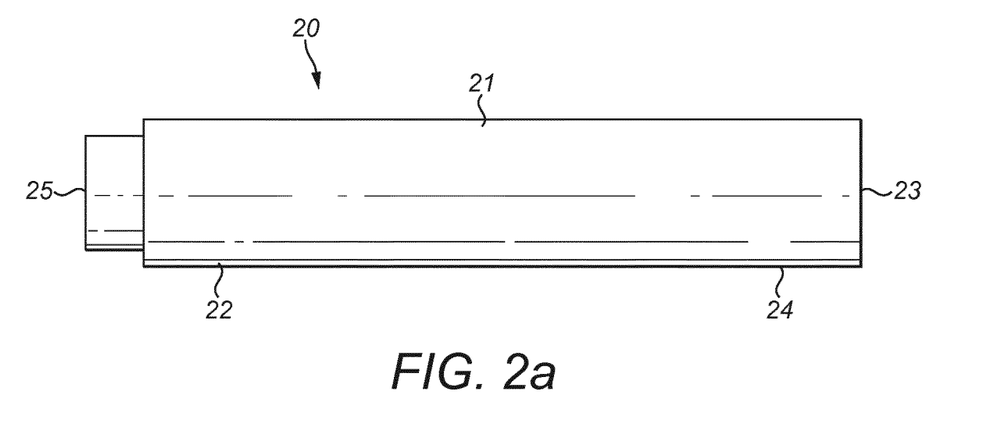
FIG. 2a is a side view of a drug delivery device containing the syringe of FIG. 1.
Figure 2B:
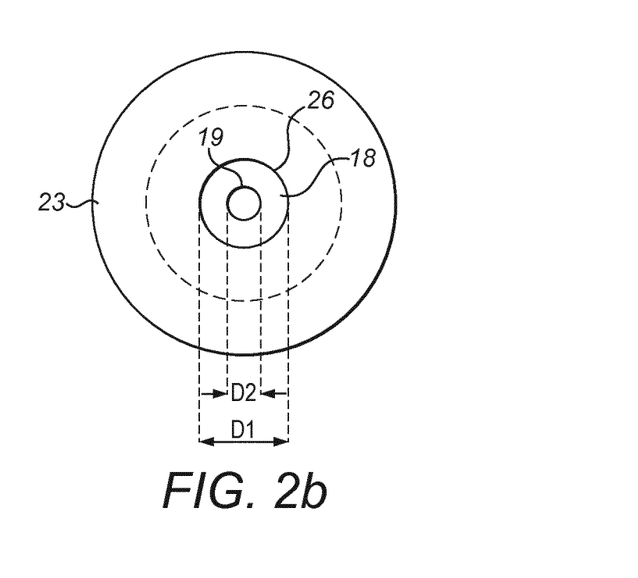
FIG. 2b is a front view of a drug delivery device containing the syringe of FIG. 1.

FIGS. 2a and 2b respectively show a side view and front view of an exemplary drug delivery device 20 containing a syringe 10. As shown in FIG. 2a, the drug delivery device 20 comprises a housing 21 configured to contain a syringe 10. The housing 21 may entirely enclose or contain the syringe 10. The housing comprises a proximal end 22 configured to be held by a user during an injection procedure, and a distal face 23 arranged at a distal end 24 of the drug delivery device 20. The distal face 23 of the drug delivery device housing 21 contacts an injection site during an injection procedure.

The drug delivery device 20 further comprises an actuating means 25 arranged on said housing 21, for instance at the proximal end 22 of said housing 21. The actuating means 25 is shown in FIG. 2a as a button, however any actuating means such as a dial or slider may be present instead. The actuating means 25, when actuated by a user, is configured to apply pressure to the stopper 16 of the syringe 10 to move the stopper from the proximal end 13 of the syringe 10 towards the distal end 14 of the syringe 10, to eject the liquid medicament 12. FIG. 2a shows the actuating means 25 arranged at the proximal end 22 of the housing, but the actuating means 25 may be arranged at a different location on the housing 21. One or more additional actuating means (not shown) may be arranged on the housing 21 to perform additional functions associated with an injection procedure, such as retracting the needle shield 17.

FIG. 2b shows the drug delivery device 20 of FIG. 2a from a front view, that is viewing the distal face 23 of the auto-injector 20. The distal face 23 comprises an opening 26 arranged on said distal face 23, through which the distal end of the cannula of the syringe 10 or drug delivery device 20 passes during an injection procedure. Prior to an injection procedure, the distal end of the cannula is within the needle shield 17 and therefore does not extend outside the housing 21 of the drug delivery device 20 via the opening 26. During an injection procedure, the needle shield 17 is retracted, for example by actuating a shield remover (not shown). As a result, the cannula now extends outside the housing 21 of the drug delivery device 20, through the opening 26 in the distal face 23, for insertion into an injection site.

As can be seen in FIG. 2b, the needle shield 17 is visible through the opening 26 in the distal face 23 of the drug delivery device housing 21. The hole 19 of the needle shield 17 and the opening 26 of the housing 21 are aligned along an axis in the longitudinal axis Z such that the hole 19 of the needle shield 17 is visible through the opening 26. An approximate position of the needle shield 17 is indicated in FIG. 2b by the dotted circle.

It is advantageous that a diameter D1 of the opening 26 is greater than a diameter D2 of the hole 19 of the needle shield 17 such that the front face 18 of the needle shield 17 is visible through the opening 26. By providing at least one identifying means arranged at the distal end of the syringe 10, in particular on the front face 18 of the needle shield 17, the identifying means is visible through the opening 26 to a user or computing device located outside the drug delivery device 20. This advantageously allows a user or computing device to easily observe the identifying means and thus identify the liquid medicament 12 contained within the container 11 of the syringe 10 without having to disassemble the drug delivery device 20 or remove the syringe 10 from within the housing 21 of the drug delivery device 20.

Figure 3A:
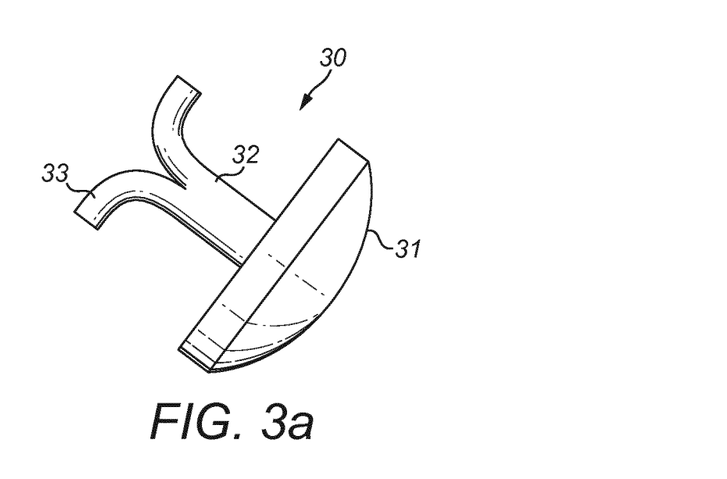
FIG. 3a is an isometric view of an identifying means comprising a pin according to an embodiment.

FIG. 3a shows an exemplary embodiment of the identifying means, in which the identifying means comprises a pin 30. The pin 30 is configured to be mounted on the front face 18 of the needle shield 17, as shown in FIG. 3b.

FIG. 3a shows the pin 30 comprising a head 31 and a protrusion 32 extending from the head 31. The protrusion 32 is configured to be inserted within the hole 19 of the needle shield 17 such that the pin 30 is mounted in the hole 19 of the needle shield 17. The head 31 of the pin 30 contacts the front face 18 of the needle shield 17 when the pin 30 is mounted in the needle shield 17 to prevent further movement of the pin 30 into the hole 19. As shown in FIG. 3a, the protrusion 32 preferably comprises at least one leg 33 configured to hold the pin 30 in the hole 19 of the needle shield 17. The pin 30 is therefore releasably attachable to the needle shield 17.

Figure 3B:
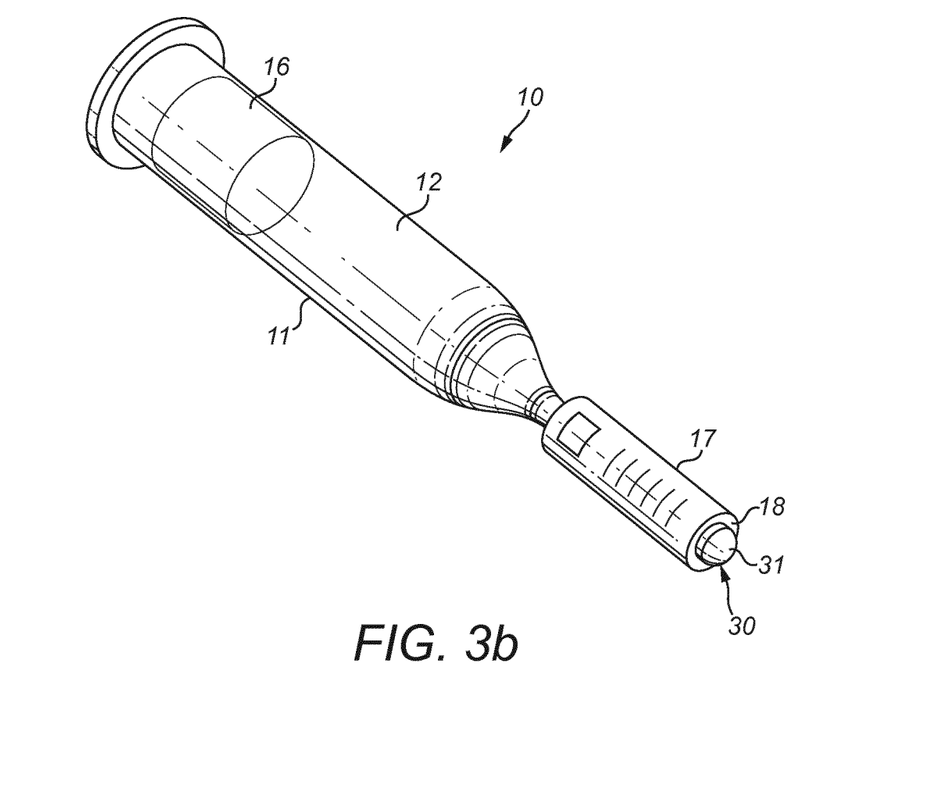
FIG. 3b is an isometric view of the pin of FIG. 3a mounted in the needle shield of a syringe according to an embodiment.

FIG. 3b shows the pin 30 mounted on the needle shield 17, in this case in the front face 18 of the needle shield 17, in the hole 19. The head 31 of the pin 30 is adjacent the front face 18 of the needle shield 17.

The pin 30 may be coloured, wherein the colour identifies the liquid medicament 12 within the syringe 10. In this way a number of different colours can be used to easily identify a number of different liquid medicaments.

The pin 30 may be mounted on the front face 18 of the needle shield 17 during assembly of the syringe 10, prior to insertion of the syringe 10 into the housing 21 of the drug delivery device 20. Once the syringe 10 has been inserted into a drug delivery device 20, the coloured pin 30 will be visible through the opening 26 in the distal face 23 of the drug delivery device 20, as previously described with reference to FIGS. 2a and 2b.

The use of a pin 30 as the identifying means is particularly advantageous in that it is relatively cheap and simple to manufacture, and can be mounted into the hole 19 of a syringe 10 with little or no modification of the syringe 10. The pin 30 is also easily visible to a user through the opening 26 of the drug delivery device 20. The liquid medicament contained 12 within a syringe 10 that has already been inserted into a drug delivery device housing 21 may therefore be easily identified without disassembling the drug delivery device 20 or removing the syringe 10 from the drug delivery device 20. By mounting the pin 30 in the hole 19 of the needle shield 17, the diameter D1 of the opening can be kept small relative to the diameter D2 of the needle shield 17, thereby preventing unnecessary exposure of the inside of the housing 21 and the components of the drug delivery device/syringe contained therein.

The pin 30 may be made of plastic or metal. Plastic is advantageous since it is relatively easy to produce pins of different colours. Metal is advantageous since it can be easily stamped and/or bent into shape, perhaps with an integrated stamped symbol. Therefore pins 30 can be cheaply and easily produced to identify a variety of liquid medicaments 12.

The pin 30 can be removed from the needle shield 17 prior to an injection procedure, for example by first removing the syringe 10 from within the housing 21 of the drug delivery device 20.

Figure 4A:
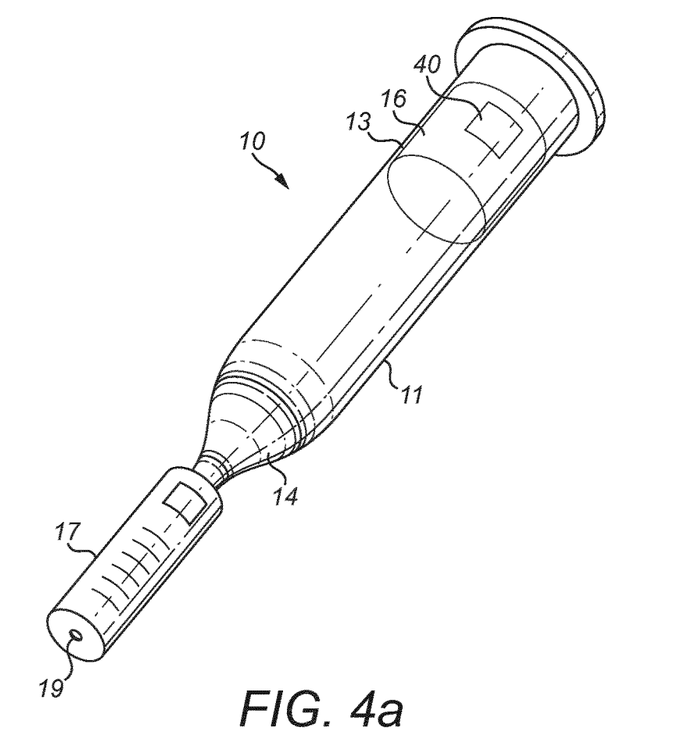
FIG. 4a is an isometric view of a syringe for use in a drug delivery device according to an embodiment, the syringe having an identifying means printed on the container of the syringe.
Figure 4B:
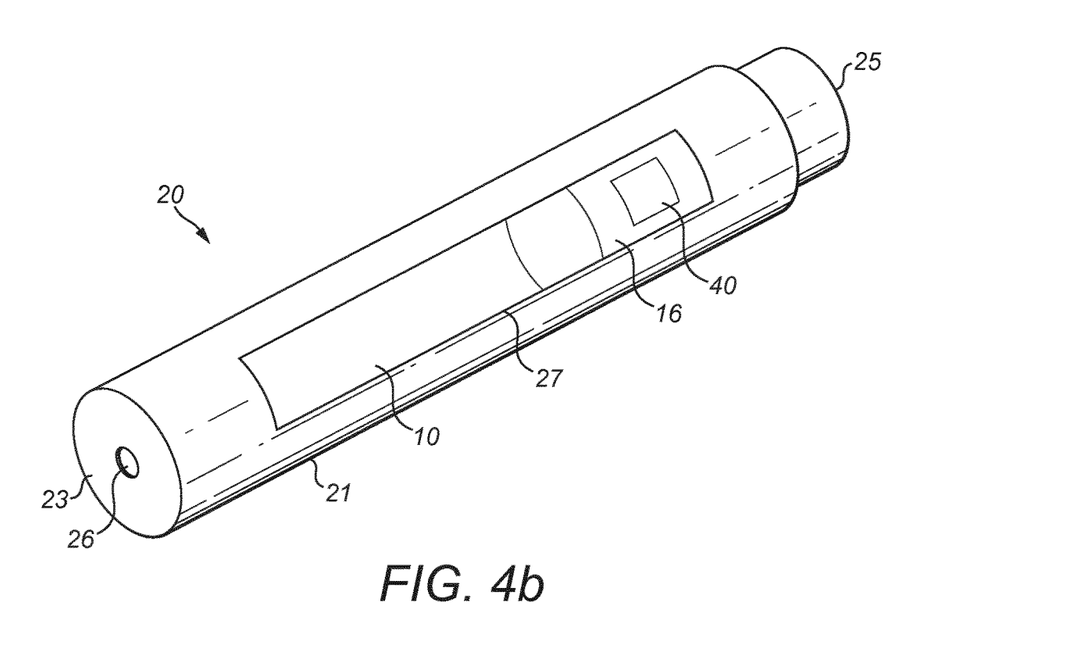

FIGS. 4a and 4b are perspective views of a drug delivery device 20 according to a further embodiment, and the syringe 10 contained within the drug delivery device 20.

FIG. 4a shows a syringe 10 that is similar to the syringe 10 previously described with reference to FIGS. 1 and 3b. The syringe 10 shown in FIG. 4a comprises a cannula (not shown) and needle shield 17, however the syringe 10 of the present embodiment may alternatively not comprise a needle shield 17. In this case the needle shield 17 may be comprised in a different part of the drug delivery device 20.

FIG. 4a shows a syringe 10 wherein the identifying means comprises a marking 40 printed on the container 11 of the syringe 10, for example on an outer surface of the container 11. In some examples the container 11 is a glass barrel and the marking 40 is printed onto the glass barrel. The marking 40 may be printed onto the container 11 using ink. Furthermore, the marking 40 may be printed by a silk-screen printing technique.

The marking 40 preferably comprises a barcode, such as a QR code or Data Matrix, so that the marking 40 is readable by a computing device.

The marking 40 may be printed on the container 11 using UV light. For example, the marking 40 may comprise a coating such as an ink cured by UV radiation.

In some embodiments, the marking 40 may be laser marked on a surface of the container 11, which may be a glass barrel. The marking may be a UV laser marking or a laser engraving as discussed previously. In some examples, the marking 40 may be a tool constrained feature. That is, the marking 40 may be a stamped feature on the container 11, such as an embossment or protrusion.

FIG. 4a shows the marking 40 arranged on an outer surface of the container 11, at the proximal end 13. The marking 40 overlays the stopper 16 when the stopper 16 is in its initial longitudinal position at the proximal end 13 of the container 11.

The marking 40 and the stopper 16 may be substantially different colours. This means the marking 40 is clearly visible to a user against the stopper 16, thereby making identification of the liquid medicament 12 easier.

Alternatively, the marking 40 and the stopper 16 may be substantially the same colour. This means the marking 40 is not clearly visible to an end user against the stopper 16. This may be advantageous when it is not desirable for the end user to notice the marking 40. If the marking 40 and the stopper 16 are substantially the same colour, the marking 40 may be readable by a computing device, for example during assembly of the syringe 10 and/or drug delivery device 20, but not easily readable by an end user. The marking 40 may become readable to an end user after an injection procedure has taken place. In other words, the marking 40 may not be clearly visible to an end user when the stopper 16 is in a first longitudinal position at the proximal end 13 of the container 11, but is visible once the stopper 16 has moved to a second longitudinal position towards the distal end 14 of the container 11.

It may be preferable that the marking comprises an ink that is not visible to the naked eye. For example, the marking may comprise a UV ink that is only visible to a human under UV light. This can help reduce counterfeiting of the syringe 10.

FIG. 4b shows another exemplary drug delivery device 20. The drug delivery device 20 is similar to the drug delivery device 20 shown in FIG. 2a but the housing 21 of the drug delivery device 20 additionally comprises a window 27 arranged at a side of the auto-injector housing 21. The syringe 10 is contained within the housing 21. The housing 21 may entirely enclose or contain the syringe 10. A syringe 10 contained within the drug delivery device housing 21 is therefore visible through the window 27. Upon actuation of the actuating means 25 by a user, the stopper 16 is moved from a first position near the proximal end of the syringe 10 to a second position nearer the distal end of the syringe 10. The window 27 in the drug delivery device housing 21 allows a user to view the movement of the stopper 16.

The marking 40 on the outer surface of a container 11 (or in some examples on the outer radial surface of a stopper 16) of a syringe 10 according to the present embodiment is also visible to a user through the window 27 of the housing 11. The marking 40 may be read by a user in order to identify the liquid medicament 12 contained within the syringe 10 without removing the syringe 10 from the drug delivery device 20 or disassembling the drug delivery device 20. In the case that the marking 40 comprises a barcode, the barcode may be readable by a camera or other scanner of a computing device in order to identify the liquid medicament 12. The camera may read the barcode during/after assembly of the syringe 10 and/or placement of the syringe 10 into the drug delivery device 20. In some examples the barcode may be readable by a camera in a portable electronic device such as a smartphone operated by an end user of the drug delivery device. Software on the portable electronic device may identify the liquid medicament 12 from the barcode.

Figure 5A:
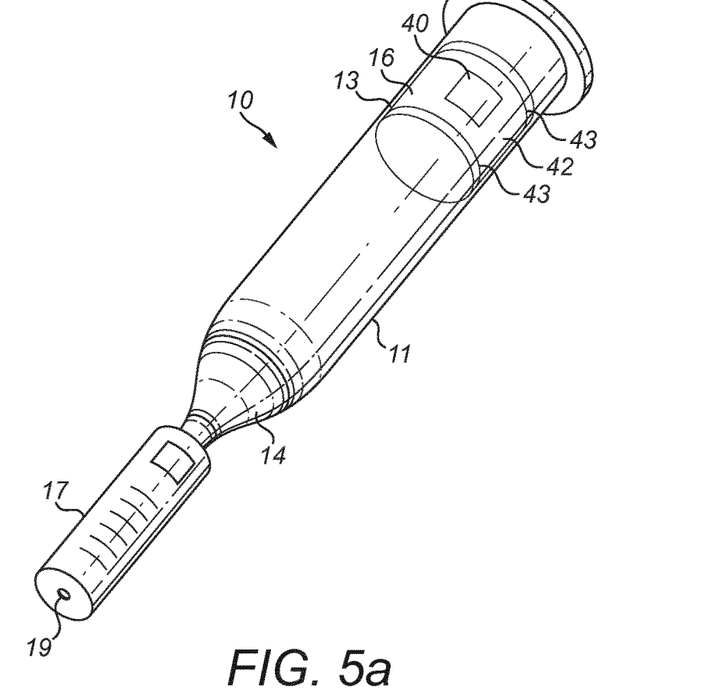
FIG. 5a is an isometric view of a syringe for use in a drug delivery device according to an embodiment, the syringe having an identifying means located on the stopper of the syringe.
Figure 5B:
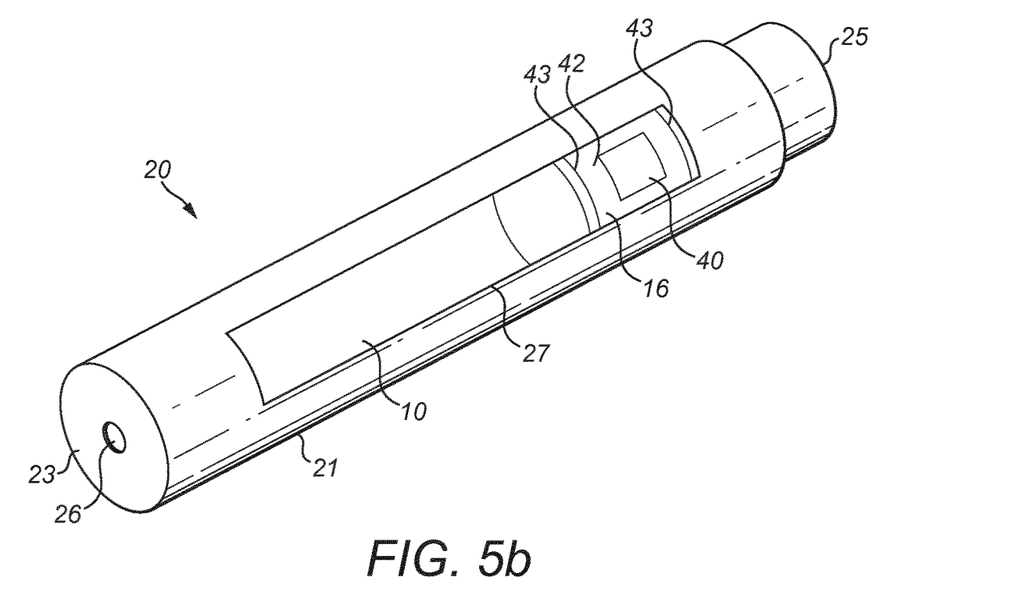

FIGS. 5a and 5b show a syringe 10 and drug delivery device 20 that are similar to the syringe 10 and drug delivery device of FIGS. 4a and 4b, except that the identifying means (in this example marking 40) is located on the stopper 16 rather than the container 11. The marking 40 may be positioned on the circumferential surface 42 of the stopper 16. As described with reference to FIGS. 4a and 4b, the marking 40 of FIGS. 5a and 5b may be a UV laser marking or a laser engraving. In some examples, the marking 40 may be a tool constrained feature. That is, the marking 40 may be a stamped feature on the circumferential surface 42 of the stopper 16, such as an embossment or protrusion. The marking 40 may comprise an ink, such as a UV ink, as discussed previously in relation to FIGS. 4a and 4b, wherein the ink has been printed onto the stopper 16. The marking 40 may be printed by a silk-screen printing technique.

As shown in FIGS. 5a and 5b, the stopper 16 has a plurality of sealing surfaces 43. These sealing surfaces 43 are circumferential ridges extending radially from the circumferential surface 42 of the stopper 16 such that they contact the inner surface of the container 11, thereby forming a seal. The marking 40 may be positioned on the circumferential surface 42 between at least two sealing surfaces 43 of the stopper 16. The marking 40 could additionally or alternatively be positioned under or around at least one sealing surface 43 of the stopper 16.

Figure 6A:
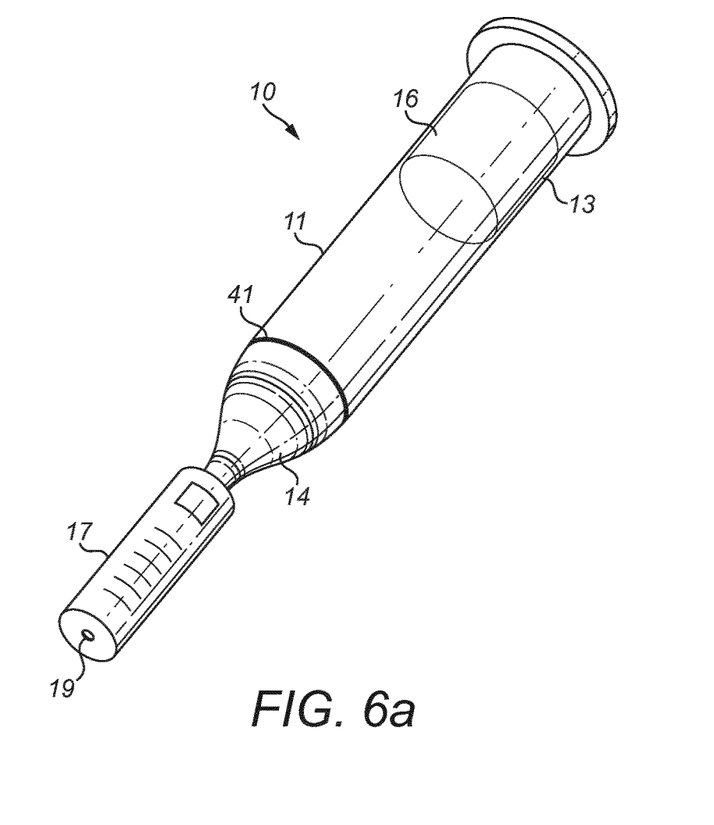
FIG. 6a is an isometric view of a syringe for use in a drug delivery device according to some embodiments, the syringe having a ring on the container of the syringe.
Figure 6B:
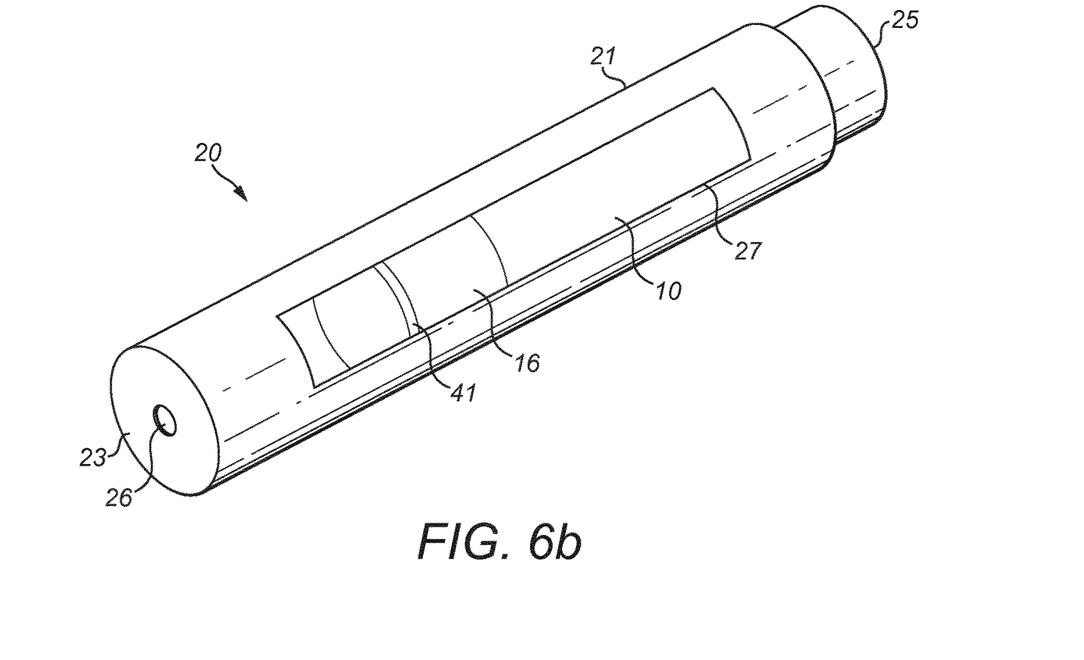

FIGS. 6a and 6b are perspective views of a drug delivery device 20 according to further embodiments, and the syringe 10 contained within the drug delivery device 20.

Like FIGS. 4a and 4b, FIGS. 6a and 6b show a syringe 10 wherein the identifying means comprises a marking printed on an outer surface of the container 11. FIG. 6a shows the syringe 10 contained within the housing 21 of the drug delivery device 20 shown in FIG. 6b. The housing 21 may entirely enclose or contain the syringe 10. It is also the case that the syringe 10 of FIGS. 6a and 6b may or may not comprise a needle shield 17, although a needle shield 17 is shown in FIG. 6a. However, FIGS. 6a and 6b show that the marking comprises a ring 41.

The ring 41 may be printed on the container 11 using UV light. For example, the ring 41 may comprise a coating cured by UV radiation.

In some embodiments, the ring 41 may be laser marked on the container 11.

The ring 41 is arranged around the outer surface of the container 11 and may encircle the outer surface of the container 11 partially or entirely. The ring 41 may be a coloured ring. The colour of the ring 41 may identify the liquid medicament 12 contained within the container 11. Alternatively or additionally, another property of the ring 41 such as the width of the ring 41 or its position on the container 11 may identify the liquid medicament 12.

The ring 41 may be located at the distal end 14 of the container 11. In particular, the ring 41 may be arranged on the container 11 such that the stopper 16 is aligned with the ring 41 after an injection procedure has been performed, as illustrated in FIG. 6b. That is, the stopper 16 is aligned with the ring 41 at a final longitudinal position at the distal end 14 of the container 11 once a desired dose of liquid medicament 12 has been delivered. In this way a user of the drug delivery device 20 can be assured that the entire dose has been delivered.

The present disclosure also relates to a method of manufacturing a drug delivery device 20 according to any of the aforementioned embodiments. In particular, the method comprises providing the syringe 10 of a drug delivery device 20 according to any of the aforementioned embodiments with at least one identifying means identifying the liquid medicament 12 contained in the container 11 of the syringe 10.

The present disclosure also relates to a method for identifying a liquid medicament contained within the syringe 10 of a drug delivery device 20 according to any of the aforementioned embodiments. In particular, the method comprises detecting, by a sensor, at least one identifying means on the syringe 10, and, in response to detecting said at least one identifying means, identifying the liquid medicament 12 contained in the container 11 of the syringe 10 using the at least one identifying means and. The method may be computer-implemented.

Identifying the liquid medicament 12 contained in the container 11 of the syringe 10 using the at least one identifying means may comprise comparing the detected at least one identifying means with a database, wherein the database may comprise the identity/identities of at least one liquid medicament. Identifying the liquid medicament may comprise determining that there is a match between the detected at least one identifying means and the identity of at least one liquid medicament stored in the database.

In some examples, the identity of the liquid medicament may be verified by comparing the detected at least one identifying means with a database, and determining that the identity of the liquid medicament is verified when the comparison with the database results in a match.

Although claims have been formulated in this application to particular combinations of features, it should be understood that the scope of the disclosure also includes any novel features or any novel combinations of features disclosed herein either explicitly or implicitly or any generalisation thereof, whether or not it relates to the same invention as presently claimed in any claim and whether or not it mitigates any or all of the same technical problems as does the present invention. The applicant hereby gives notice that new claims may be formulated to such features and/or combinations of features during the prosecution of the present application or of any further application derived therefrom.

Although several embodiments have been shown and described, it would be appreciated by those skilled in the art that changes may be made in these embodiments without departing from the principles of the invention, the scope of which is defined in the claims.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, $15^{th}$ edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N—(ω-carboxyheptadecanoyl)-des(B30) human insulin and B29-N—(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. Volumes of medicament delivered with these various devices can range from about 0.5 ml to about 2 ml.

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

The invention claimed is:
1. A drug delivery device comprising:
   a housing comprising an opening extending from an outer surface of the housing to an inner surface of the housing; and
   a syringe contained in the housing, the syringe comprising:
      a container containing a liquid medicament, the container comprising an aperture at a distal end thereof and through which the liquid medicament can be dispensed;
      a stopper within the container, the stopper moveable between a first longitudinal position and a second longitudinal position relative to the container to cause dispensing of the liquid medicament through the aperture;

a needle shield configured to surround a cannula, wherein the needle shield is movable towards the container to expose a distal tip of the cannula through a hole of the needle shield; and at least one identifier identifying the liquid medicament, wherein the at least one identifier is arranged on the needle shield and located inside the housing such that the at least one identifier is visible through the opening of the housing, and wherein the at least one identifier is configured to move with the needle shield when the needle shield moves with respect to the container.

2. The drug delivery device of claim 1, wherein the liquid medicament is to be dispensed through the hole, and wherein the at least one identifier is arranged on an outer surface of the needle shield.

3. The drug delivery device of claim 2, wherein the at least one identifier comprises a pin mounted on the needle shield.

4. The drug delivery device of claim 3, wherein the pin is mounted in the hole of the needle shield.

5. The drug delivery device of claim 4, wherein the pin comprises a head and a protrusion arranged on the head, wherein the protrusion is configured to be mounted in the hole of the needle shield.

6. The drug delivery device of claim 2, wherein the outer surface of the needle shield comprises a front face, wherein the hole is arranged on the front face, and wherein the at least one identifier is arranged on the front face.

7. The drug delivery device of claim 2, wherein the at least one identifier comprises a printed surface.

8. The drug delivery device of claim 1, wherein the at least one identifier is arranged at a distal end of the syringe.

9. The drug delivery device of claim 1, wherein the at least one identifier comprises a marking.

10. The drug delivery device of claim 9, wherein the marking is printed using UV light or by laser marking.

11. The drug delivery device of claim 9, wherein the marking comprises a barcode.

12. The drug delivery device of claim 1, wherein a proximal end of the housing extends proximal to a proximal end of the needle shield.

13. The drug delivery device of claim 1, wherein an inner diameter of the housing is greater than an outer diameter of the needle shield.

14. The drug delivery device of claim 1, wherein the housing encloses both the needle shield and the at least one identifier.

15. The drug delivery device of claim 1, wherein the distal tip of the cannula is configured to pass through the opening of the housing and the hole of the needle shield during an injection.

16. The drug delivery device of claim 1, wherein the opening of the housing is located on a distal face of the housing, and the distal face is configured to contact a user's skin during an injection.

17. The drug delivery device of claim 1, wherein the hole of the needle shield is aligned with the opening of the housing.

18. The drug delivery device of claim 1, wherein the hole of the needle shield is concentric with the opening of the housing.

19. A method of manufacturing a drug delivery device that includes a housing comprising an opening extending from an outer surface of the housing to an inner surface of the housing, and a syringe contained in the housing, wherein the syringe comprises:

a needle shield configured to surround a cannula; and a container containing a liquid medicament, the container comprising an aperture at a distal end thereof and through which the liquid medicament can be dispensed, and a stopper within the container, the stopper moveable between a first longitudinal position and a second longitudinal position relative to the container to cause dispensing of the liquid medicament through the aperture, wherein the needle shield is movable towards the container to expose a distal tip of the cannula through a hole of the needle shield;

wherein the method comprises providing the syringe with at least one identifier identifying the liquid medicament contained in the container such that the at least one identifier is arranged on the needle shield and located inside the housing such that the at least one identifier is visible through the opening of the housing and the at least one identifier is configured to move with the needle shield when the needle shield moves with respect to the container.

20. A method for identifying a liquid medicament contained within a drug delivery device, the method comprising:

detecting, by a sensor, at least one identifier on a syringe contained in a housing of the drug delivery device, the housing comprising an opening extending from an outer surface of the housing to an inner surface of the housing, the at least one identifier being arranged on a needle shield of the drug delivery device and located inside the housing such that the at least one identifier is visible through the opening of the housing, the needle shield configured to surround a cannula and movable towards a container of the syringe to expose a distal tip of the cannula through a hole of the needle shield, the at least one identifier configured to move with the needle shield when the needle shield moves with respect to the container; and in response to detecting the at least one identifier, identifying the liquid medicament using the detected at least one identifier.

* * * * *